United States Patent [19]

Hashiguchi et al.

[11] Patent Number: 4,520,130

[45] Date of Patent: May 28, 1985

[54] HALOSILANE CATALYST AND PROCESS FOR MAKING SAME

[75] Inventors: Don H. Hashiguchi, University Heights; Erhard Klar, Beachwood; Ronald J. Dietrich, Strongsville, all of Ohio

[73] Assignee: SCM Corporation, New York, N.Y.

[21] Appl. No.: 608,293

[22] Filed: May 8, 1984

[51] Int. Cl.$^3$ .......................... B01J 23/14; B01J 23/72
[52] U.S. Cl. ..................................... 502/345; 556/476
[58] Field of Search ............... 502/331, 345, 346, 352; 241/14; 556/476

[56] References Cited

U.S. PATENT DOCUMENTS 2,443,902  6/1948  Ferguson et al. ............... 502/345 X
2,889,350  6/1959  Horny et al. ................... 502/346 X Primary Examiner—W. J. Shine
Attorney, Agent, or Firm—R. A. Sturges; T. M. Schmitz

[57] ABSTRACT

An improvement in process for making cupreous catalyst composition, wherein a copper oxide-preponderant grind charge derived from the oxidation of elemental copper and/or an alloy thereof is subject to high energy milling with concomitant crystal lattice distortion until the average particle of the resulting grind is no larger than about 20 microns, comprises establishing a tin concentration between about 400 and about 3000 ppm in said composition prior to or after said high energy milling. The resulting catalyst is useful for producing organohalosilane from alkyl chloride and silicon.

8 Claims, No Drawings

HALOSILANE CATALYST AND PROCESS FOR MAKING SAME

This application is related to these having the following Ser. Nos.: 548,604 of Nov. 4, 1983, now abandoned; 574,809 filed Jan. 30, 1984, now U.S. Pat. No. 4,504,596; 580,595 filed Feb. 16, 1984, now U.S. Pat. No. 4,504,597; and 597,853 filed Apr. 9, 1984, now U.S. Pat. No. 4,503,165. The teachings of these applications are incorporated herein expressly by reference.

This invention relates to particulate cupreous catalyst and a method for making same, and more particularly to this sort of catalyst for producing an alkyl or aryl halosilane (such as dimethyldichlorosilane from methyl chloride and silicon) at elevated temperature.

BACKGROUND OF THE INVENTION

A variety of cupreous catalysts have been proposed for such silane production. Heretofore the ones in most general use had appreciable precipitated copper content. Accordingly, they often were contaminated with noncupreous material in proportions not always easy to control. The instant invention enables the metallurgists to make a catalyst of good activity more reproducibly using copper oxide-rich starting materials prepared by pyrometallurgy.

BROAD STATEMENT OF THE INVENTION

One aspect of the instant invention is an improvement in process for making cupreous catalyst composition wherein a copper oxide-preponderant grind charge derived from the oxidation of elemental copper and/or an alloy thereof is subject to high energy milling with concomitant crystal lattice distortion until the average particle size (mass median diameter) of the resulting grind is no larger than about 20 microns. The improvement comprises establishing a tin concentration between about 400 and about 3000 ppm in said composition prior to or after said high energy milling.

Another aspect of the instant invention is a pyrometallurgically-sourced particulate catalyst composition for organohalosilane production, said composition consisting essentially of a major proportion of cuprous and cupric oxides, a minor proportion of elemental copper, containing tin in a proportion of about 400–3000 ppm, having particle size not substantially above about 20 microns, and exhibiting crystal lattice distortion.

DETAILED DESCRIPTION OF THE INVENTION

For efficiency and economy the cupreous particulates providing the grind charge (i.e. the charge to the high energy milling operation) generally are no larger than about 80 mesh, advantageously −150 mesh, and preferably preponderantly −325 mesh (so such charge will not unduly restrict production in the high energy milling operation). Average particle size of such grind charge is above 20 microns and ordinarily 90% or more of it will be at least 25 microns or coarser. Desirably these particulates should not contain more than about 3 percent of adventitious (that is, normally or inherently present, but not deliberately added) material for best control of charge analysis. The grind charge desirably is extremely low in lead and other impurities that are considered detrimental for silane catalysts.

The grind charge can contain, if desired, up to about 10% and usually just a few percent of promoter-providing material such as elemental zinc, iron, or the oxides or chlorides of these metals, copper chloride, even a little antimony (below 0.05%), and silica or aluminosilicates typically up to a few percent maximum. The promoter can be an original part of the grind charge of cupreous particulates, or it can be added thereto prior to or after the high energy comminution that follows. In some instances it can be efficient to add a promoter-providing material such as iron and/or other metal as particles of an alloy of such metal with at least part of the particulate copper that is to be further processed by pyrometallurgy (e.g. oxidation) to make such grind charge for the high energy milling.

The tin concentration in the catalyst can be established in one or more of a variety of ways. One can alloy at least a part of it or simply blend at least a part of it with the copper or copper alloy, e.g. powder, that is to be oxidized. Another way is to add at least a part of it as elemental metal (or a tin-bearing material such as an oxide, or sulfide or chloride or copper/tin alloy powder) to the grind charge for the high energy milling or even to a preparatory milling stage such as hammermilling. Still another way is to add at least a part of such tin-bearing material to the grind that results from the high energy milling.

The tin concentration in the catalyst is reckoned as the fraction equivalent in weight to elemental tin whether such tin is in combined form or not. It may operate to keep the catalyst more free-flowing in use, or it may act to form sites that are beneficially attacked by a reactant such as a chloride in the halosilane manufacture. Whether the enhancement of catalyst is due to one of these or some other reason is not known.

In a cuprous oxide-rich catalyst tin incorporation advantageously is from about 400–1800 ppm and preferably 900–1800 ppm. Typically the copper stoichiometry of such catalyst is 65–95% cuprous oxide, 2–28% cupric oxide, and 2–15% elemental copper.

In a catalyst richer in cupric oxide and elemental copper tin incorporation advantageously is about 400–2500 ppm and preferably 900–2500 ppm. Typically the copper stoichiometry of such catalyst is 30–65% cuprous oxide, 28–45% cupric oxide, and 4–25% elemental copper.

By a pyrometallurgically-sourced catalyst composition is meant that the cupreous material going into the grind charge is made by heating copper metal and/or a copper compound such as a copper oxide or carbonate in an inert and/or a chemically reactive atmosphere (usually a reducing or an oxidizing one) or in the substantial absence of any atmosphere. One typical source of such cupreous material is the mill scale that forms on the surfaces of hot copper ingots that are exposed to air; another is from the air-oxidized surfaces of copper machining chips and cuttings; another is the controlled air oxidation of copper particles; still another is from the collection of vaporized copper and/or dusts of an oxide of copper. Such cupreous material for making a grind charge can be from a single pyrometallurgical source as, for example, the air oxidation of fine copper particles. Alternatively it can be a blend of products from a plurality of pyrometallurgical sources.

The stoichiometry (proportions) of the catalyst with respect to cuprous oxide, cupric oxide, and elemental copper can be manipulated effectively by blending various oxidized copper materials when necessary or desirable. In one very useful embodiment the grind charge simply is hammermilled cuprous oxide-rich particulates (typically about 85–90% cuprous oxide). If greater cupric oxide is desired, that material can be roasted in air. Another way to make stoichiometric adjustments is to blend such cupric oxide-enriched roasted material with the reroasted admixture of some of the first mentioned cuprous oxide-rich hammermilled material and some particulate copper metal.

The grind charge advantageously has been comminuted previously to fairly small size in a mill with a short retention time such as a hammermill using swing or fixed hammers. Other conventional pulverizing apparatus also can be used for such operation preparatory to the high energy milling. Thus, one can use a roller mill, an attrition mill, or a fluid energy mill.

Especially advantageous for the instant process is the careful selection of a grind charge of analysis as outlined herein coupled with the fineness of grind made by the energy comminution of such charge (to give adequate surface area and crystal lattice distortion to the catalyst product). Desirably such comminution is operated continuously, that is, with continuous feed to and take-off from the high energy milling (comminuting) apparatus. Batch milling can be used for this step if desired, however. Illustrative of a useful batch mill is the Sweco (the trademark of Sweco, Inc.) vibratory mill. A continuous high energy comminution apparatus preferred is a so-called "Palla mill", the product of Humboldt-Wedag of West Germany. A smaller laboratory size batch vibratory mill that can be useful is the Megapac (a trademark of Pilamec Ltd.) mill. Such mills generally are called "vibratory ball mills"—although the grinding media inside the shell(s) is often other than spherical in shape. Such media typically is made of a hard ceramic (such as alumina, zirconia), a steel (such as a stainless steel, a low alloy steel, a nickel steel), tungsten carbide, etc., all conventional grinding media. Such mill generally oscillates with a compound motion that is imparted to the shell(s) by an eccentric mechanism.

Another high energy mill useful for the instant purpose is the "Szegvari mill" made by the Union Process Company. It is basically a stirred ball mill, and it even can be modified in accordance with the precepts of U.S. Pat. No. 3,927,837. In summary, the high energy comminution in the instant process is done by an apparatus that has solid grinding media in it, is driven with substantially more horsepower per unit weight of grinding medium than is a conventional tumbling ball mill, and provides a prolonged residence time (actually an average residence time in a continuous operation) for the grind charge typically of at least about 10 minutes to an hour or even longer if necessary or desired.

In a matter of a half hour to an hour a large high energy mill can comminute the grind charge to size much smaller than 10 microns average size, usually 2-7 microns. If additional size reduction is needed, the output can be recycled for remilling.

In an advantageous processing operation for making the catalyst the grind charge has particle size no coarser than 150 mesh, and the particulates thereof contain about 65–95% cuprous oxide, about 2–28% cupric oxide, and about 2–15% elemental copper.

In another useful processing operation for making the catalyst the grind charge has at least about 95% of its particles not substantially larger than 325 mesh and the particulates charged contain about 30–65% cuprous oxide, about 28–45% cupric oxide, and about 4–25% elemental copper. To obtain the particular stoichiometry of such charge it is often necessary to blend two or more powders of differing oxide and elemental copper contents.

The following examples show how the invention has been practiced, but should not be construed as limiting the invention. In this specification all parts are parts by weight, all percentages are weight percentages, all temperatures are in degrees Celsius, and all mesh sizes are U.S. Standard Sieve sizes unless otherwise expressly noted; additionally, in this specification an average particle size means the mass median particle size as measured with the Microtrac (a trademark of Leeds & Northrup Company) or the Hiac PA-720 (Hiac is a trademark of Pacific Scientific Company) particle size analyzers, and Specific Surface Area (SSA) is measured by the BET (Brunauer, Emmett, and Teller) method. In general, the catalyst particles have a specific surface area in the range of $\frac{1}{2}$ to 8 $m^2$/gram, and more specifically in the range of 2 to 8 $m^2$/gram.

EXAMPLE 1

Copper alloy particles containing 1200 ppm tin and 660 ppm aluminum were air-oxidized at elevated temperature to a copper oxide-rich condition. The resulting oxidate was pulverized to make a particulate grind charge (−150 mesh) for high energy comminution. The grind charge was milled in a Megapac TM laboratory batch mill for about 6 hours to produce particles having average particle size of 3.9 microns (mass medium diameter as measured by the Microtrac instrument). The Specific Surface Area was 2.4 $m^2$/gm., and crystal lattice distortion occurred. Stoichiometry was 39.2% cuprous oxide, 44% cupric oxide, and 16.8% elemental copper.

The particles had good activity and high selectivity as a catalyst for the reaction of methyl chloride with silicon to produce dimethyldichlorosilane. Both the activity and selectivity were markedly higher for this catalyst than for a related comparable one where the tin content was about a fourth as much. The stoichiometry of such related catalyst was 51.3% cuprous oxide, 36.6% cupric oxide, 10.5% elemental copper, and it had Specific Surface Area of 2.5 $m^2$/gm.

EXAMPLE 2

Copper particles containing 1700 ppm tin were air-oxidized at elevated temperature to a copper oxide-rich condition. The resulting oxidate was pulverized to make a particulate grind charge (−150 mesh) for high energy comminution. The grind charge was milled at about 15 kg. per hour using a Model 20U Palla mill for about a half hour average residence time to produce particles having average particle size of 5.4 microns (mass median diameter as measured by the Hiac instrument). The Specific Surface Area of the resulting catalyst was 2.8 $m^2$/gm., and crystal lattice distortion occurred. Stoichiometry was 70.1% cuprous oxide, 20.0% cupric oxide, and 9.5% elemental copper.

The particles had good activity and selectivity as a catalyst for the reaction of methyl chloride with silicon to produce dimethyldichlorosilane. The activity was markedly higher for this catalyst than for a related one comminuted with a larger (35U) Palla mill where the tin content was slightly less than a fifth as much. The stoichiometry of such related catalyst was 63.5% cuprous oxide, 27.4% cupric oxide, 9.3% elemental copper, and it had Specific Surface Area of 3.2 $m^2$/gm. The average particle size of such catalyst (measured with the Microtrac instrument) was 3.9 microns.

Frequently there is an exchange of oxygen in the grind charge undergoing high energy comminution. In such exchange cuprous oxide content usually increases while the cupric oxide and elemental copper proportions decrease. Accordingly, such comminution can be looked upon not only as a way of subdividing the particles and inducing crystal lattice distortion in the product, but also of further adjusting stoichiometry of the product.

What is claimed is:

1. A pyrometallurgically-sourced particulate catalyst composition for organohalosilane production, said composition consisting essentially of a major proportion of cuprous and cupric oxides, a minor proportion of elemental copper, containing tin in a proportion of about 400–3000 ppm, having average particle size not substantially above about 20 microns, and exhibiting crystal lattice distortion.

2. The catalyst of claim 1 wherein the cuprous oxide is about 65–95%, the cupric oxide is about 2–28%, the elemental copper is about 2–15%, the specific surface area is about $\frac{1}{2}$–8 $m^2$/gm., and the tin content is about 900–1800 ppm.

3. The catalyst of claim 1 wherein the cuprous oxide is about 30–65%, the cupric oxide is about 28–45%, the elemental copper is about 4–25%, the specific surface area is about 2–8 $m^2$/gm., and the tin content is about 400–2500 ppm.

4. In a process for making cupreous catalyst composition consisting essentially of a major proportion of cuprous and cupric oxides and a minor proportion of elemental copper wherein a copper oxide-preponderant grind charge derived from the oxidation of elemental copper and/or an alloy thereof is subjected to high energy milling until the average particle size of the resulting grind is no larger than about 20 microns, the improvement which comprises: establishing a tin concentration between about 400 and about 3000 ppm in said composition prior to or after said high energy milling, said catalyst composition being further characterized by crystal lattice distortion.

5. The process of claim 4 wherein at least a part of said tin is an alloying component of the copper that is oxidized.

6. The process of claim 4 wherein at least a part of said tin is blended in the form of elemental tin or a tin-bearing compound with the copper to be oxidized.

7. The process of claim 4 wherein at least a part of said tin is added as elemental metal or tin-bearing compound or alloy to said grind charge.

8. The process of claim 4 wherein at least a part of said tin is added as elemental metal or tin-bearing compound or alloy to the grind resulting from said high energy milling.

* * * * *